(12) United States Patent
Briggs et al.

(10) Patent No.: US 6,749,584 B2
(45) Date of Patent: Jun. 15, 2004

(54) BALLOON PROTECTOR SLEEVE

(75) Inventors: Leonard F. Briggs, Chula Vista, CA (US); Tom Steinke, San Diego, CA (US)

(73) Assignee: Reva Medical, Inc., San Diego, CA (US)

( * ) Notice: Subject to any disclaimer, the term of this patent is extended or adjusted under 35 U.S.C. 154(b) by 210 days.

(21) Appl. No.: 10/010,787

(22) Filed: Nov. 9, 2001

(65) Prior Publication Data

US 2003/0093086 A1 May 15, 2003

Related U.S. Application Data

(60) Provisional application No. 60/313,134, filed on Aug. 17, 2001.

(51) Int. Cl.[7] ........................ A61M 31/00; A61M 37/00; A61M 25/00; A61M 5/32; A61F 2/06
(52) U.S. Cl. ................. 604/103.05; 604/265; 606/194; 623/1.12
(58) Field of Search ................. 604/93.01, 96.01, 604/103.05, 171, 172, 264, 265, 523; 606/108, 192, 194, 195, 198; 623/1.11, 1.12, 1.18, 1.19, 1.2

(56) References Cited

U.S. PATENT DOCUMENTS

| | | | |
|---|---|---|---|
| 5,015,231 A | 5/1991 | Keith et al. |
| 5,290,306 A | 3/1994 | Trotta et al. |
| 5,352,236 A | 10/1994 | Jung et al. |
| 5,417,707 A | 5/1995 | Parkola |
| 5,425,709 A | 6/1995 | Gambale |
| 5,569,294 A | 10/1996 | Parkola |
| 5,584,852 A | 12/1996 | Parkola |
| 5,735,869 A | 4/1998 | Fernandez-Aceytuno |
| 5,749,852 A | 5/1998 | Schwab et al. |
| 5,762,996 A | 6/1998 | Lucas et al. |
| 5,868,707 A | 2/1999 | Williams et al. |
| 5,997,562 A | 12/1999 | Zadno-Azizi et al. |
| 6,132,450 A | 10/2000 | Hanson et al. |
| 6,152,944 A | 11/2000 | Holman et al. |

*Primary Examiner*—Brian L. Casler
*Assistant Examiner*—Mark K Han
(74) *Attorney, Agent, or Firm*—Knobbe, Martens, Olson & Bear, LLP

(57) ABSTRACT

A protector sleeve is disclosed for protecting an expandable member disposed on a catheter during pre-deployment handling. In one embodiment, the protector sleeve includes a tubular member with proximal and distal portions and preferably an elastomer seal therebetween, wherein the proximal portion of the tubular member is designed to slidably engage the expandable member in its collapsed state, while the distal portion permits fluid access to a catheter lumen, e.g., a guidewire lumen, without exposing the protected expandable member to the fluid.

8 Claims, 4 Drawing Sheets

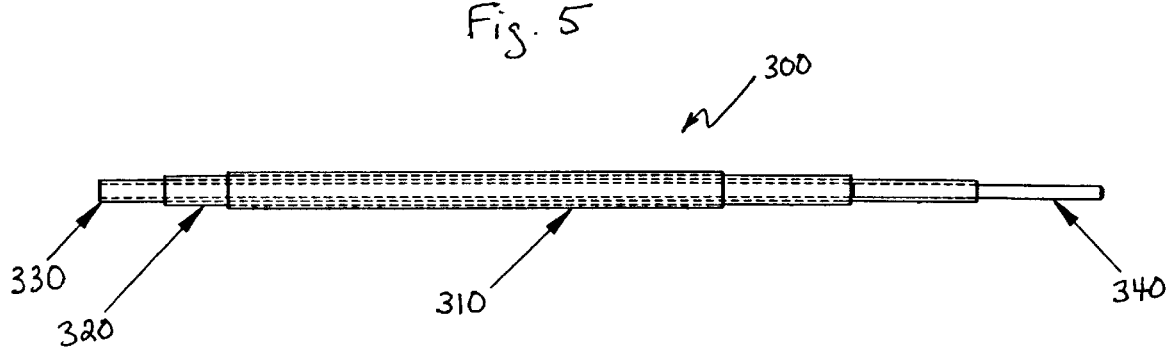

BALLOON PROTECTOR SLEEVE

RELATED APPLICATIONS

This application claims priority under 35 U.S.C. §119(e) to U.S. Provisional Application No. 60/313,134 filed on Aug. 17, 2001.

BACKGROUND OF THE INVENTION

1. Field of the Invention

In one aspect of the present invention, a protector sleeve is disclosed for protecting a pre-deployed, expandable member in its collapsed state on a catheter. Preferably, the protector sleeve facilitates flushing of a catheter lumen, e.g., a guidewire lumen, and/or immersion of the catheter assembly in a liquid, without exposing the expandable member to the liquid.

2. Description of the Related Art

Angioplasty is an efficient and effective method for opening stenoses in the coronary artery and other parts of the vascular system. Dilatation balloon catheters are used in the treatment. The catheter is positioned at the location of a blockage and a balloon is inflated by supplying a fluid under pressure through an inflation lumen to the balloon, causing stretching of the artery and pressing of the lesion into the artery wall to re-establish acceptable blood flow through the artery.

The profile of the dilatation balloon catheter, which is determined by the outer diameter of the distal end portion of the balloon, is an important characteristic. To move through the artery, the deflated balloon diameter should be as small as possible. The core or inner tube diameter of the catheter should be minimized along with the balloon, which can be done by folding, wrapping or twisting the balloon to achieve the smallest profile possible or by reducing wall thicknesses, to the extent possible, of the balloon itself. This deflated diameter affects the ease and ability of the dilatation catheter to pass through a guide catheter and through the coronary arteries leading to the stenosis to be opened.

In order to keep the outer diameter of the balloon catheter in its deflated condition, it is common to use a balloon protector. A balloon protector protects the balloon and distal tip of the catheter from possible damage during storage and keeps the balloon tightly wrapped in its deflated condition to minimize the outer diameter of the balloon in its deflated state. During the sterilization process, the catheter, with the balloon protector in place, is exposed to an elevated temperature for a period of time which causes the balloon to be heat set in the folded or wrapped configuration in which it is held by the balloon protector. This heat setting of a balloon gives the balloon a memory so that when it is inflated and deflated during an angioplasty procedure, the deflation will cause the balloon to return to its tightly wrapped heat set shape. This heat set shape will give the balloon a low profile diameter which will help when moving the catheter to a new stenosis or removal of the catheter after the procedure has been performed.

Some current balloon protectors are tubular units made of TEFLON, the inner diameter varying along the length of the tube so as to provide adequate compression at both the proximal and distal cones, the marker band area, and remaining areas of the balloon. These TEFLON balloon protectors may be made by heat shrinking a TEFLON tube down around a mandrel, resulting in a protector having some variability in size. A problem with such protectors is that in combination with the inherent variability in balloon size in any group of catheters, the variance in the balloon protector may be large enough that all the balloon protectors will not fit any given catheter; the protector must instead be individually selected from the group to fit the catheter.

During some interventional procedures, it is desirable to flush the interior of a catheter with liquids that may provide lubrication, or procedure specific actions such as anticoagulation. These liquids may be applied with a syringe, with or without, a needle attached. Typical fluid application can be from distal to proximal, or proximal to distal depending on the type of catheter or operator preference.

Oftentimes, fluid enters the space between the catheter and the balloon protector through capillary action of the liquid. Capillary action is the attraction of the surface of a liquid to the surface of a solid, which either elevates or depresses the liquid depending upon molecular surface forces. Capillary action is a physical effect caused by the interactions of a liquid with the walls of a thin tube. The capillary effect is a function of the ability of the liquid to wet a particular material. One gets the same effect for pores and narrow spaces in any hydrophilic object. A narrow tube coated with a hydrophobic substance (such as TEFLON) should not show a capillary effect.

Balloons maybe damaged when the exterior balloon area of a catheter comes in contact with a fluid before deployment. Wetting may occur when systems are submerged in a liquid prior to deployment and/or when the catheter is flushed with liquids prior to deployment. Tools used during flushing may also contact the balloon area and either damage the balloon or damage and/or dislodge devices attached to the balloon.

Thus, there is a need for a simple protector sleeve for protecting an expandable member mounted on a catheter from damage due to exposure to moisture during pre-deployment handling.

SUMMARY OF THE INVENTION

In one embodiment, a protector sleeve is disclosed for protecting a radially collapsed expandable member mounted along a distal end portion of a catheter which has an inner lumen. The protector sleeve comprises a tubular member having proximal and distal portions The proximal portion is adapted to slidably engage the distal end portion of the catheter and cover the collapsed expandable member, wherein a coaxial separation between the proximal portion of the tubular member and the collapsed expandable member is sized to substantially prevent liquids from entering the coaxial separation. The distal portion of the tubular member defines a passageway adapted to fluidly couple with the inner lumen of the catheter, such that the inner lumen may be flushed with a liquid while the collapsed expandable member remains substantially dry.

In a variation to the above-described invention, the tubular member of the protector sleeve is made from a material selected from the group consisting of TEFLON, silicones, parylene, and other hydrophobic materials known in the art.

The tubular member may be tapered along the distal portion. The proximal portion of the tubular member is preferably longer than the collapsed expandable member. Further, the tubular member preferably has an inner surface that is coated with a hydrophobic material. In one aspect, the tubular member may be chemically modified to repel water molecules.

In one preferred mode of the protector sleeve, the proximal and distal portions of the tubular member are made from a single continuous material. The tubular member may also comprise a seal between the proximal and distal portions.

The tubular member and the seal may be formed by extrusion. Alternatively, the tubular member and the seal may be molded.

The collapsed expandable member for which the protector sleeve is designed to protect may comprise an inflatable balloon in a radially collapsed state. Alternatively, the collapsed expandable member may comprise an expandable stent in a radially collapsed state. Alternatively, the collapsed expandable member may comprise an expandable stent or graft mounted over an expansion actuator, such as an inflatable balloon.

In another preferred embodiment of the present invention, a protector sleeve is disclosed for protecting an expandable member on a catheter having an inner lumen and a distal tip, wherein the expandable member is in a collapsed state prior to deployment. The protector sleeve comprises a tubular member having proximal and distal portions and a sealing member therebetween. The proximal portion is adapted to slidably engage the catheter and cover the collapsed expandable member, wherein a coaxial separation between the proximal portion of the tubular member and the collapsed expandable member is sized to substantially prevent liquids from entering the coaxial separation. The sealing member is adapted to engage the distal tip of the catheter, such that a substantially fluid-tight seal is created between the sealing member and the distal tip. The distal portion of the tubular member defines a passageway adapted to fluidly couple with the inner lumen of the catheter, such that the inner lumen may be flushed with a liquid while the collapsed expandable member proximal to the sealing member remains substantially dry.

The sealing member may comprise an elastomer seal. Further, the proximal and distal portions of the tubular member and the sealing member may be formed from a single continuous material. Preferably, the distal portion of the tubular member is sufficiently long to prevent a flushing device from contacting the distal tip of the catheter.

The protector sleeve is preferably used where the collapsed expandable member comprises an inflatable balloon in a radially collapsed state. Alternatively, the collapsed expandable member may comprise a expandable stent in a radially collapsed state. Alternatively, the collapsed expandable member may comprise an expandable stent or graft mounted over an expansion actuator, such as an inflatable balloon.

Also disclosed is a method for protecting an expandable member mounted on a catheter having an inner lumen and a distal tip, wherein the expandable member is in a collapsed state prior to deployment. The method comprises providing a protector sleeve comprising a tubular member having proximal and distal portions and a sealing member therebetween, wherein the sealing member is adapted to engage the distal tip of the catheter, such that a substantially fluid-tight seal is created between the sealing member and the distal tip, and wherein the distal portion of the tubular member defines a passageway adapted to fluidly couple with the inner lumen of the catheter, such that the inner lumen may be flushed with a liquid while the collapsed expandable member proximal to the sealing member remains substantially dry. The protector sleeve is slid over the collapsed expandable member, such that the distal tip of the catheter engages the sealing member.

In one preferred variation to the disclosed method, a portion of a flushing device may be inserted into the passageway of the distal portion. The inner lumen of the catheter may then be flushed.

In another variation of the protector sleeve, a pre-deployment protector sleeve is disclosed for protecting a soluble polymeric coating applied to a portion of a catheter having an inner lumen and a distal tip. The protector sleeve comprises a tubular member having proximal and distal portions and a sealing member therebetween. The proximal portion is adapted to slidably engage the catheter and cover the polymeric coating, wherein a coaxial separation between the proximal portion of the tubular member and the polymeric coating is sized to substantially prevent liquids from entering the coaxial separation. The sealing member is adapted to engage the distal tip of the catheter, such that a substantially fluid-tight seal is created between the sealing member and the distal tip. The distal portion of the tubular member defines a passageway adapted to fluidly couple with the inner lumen of the catheter, such that the inner lumen may be flushed with a liquid while the polymeric coating proximal to the sealing member remains substantially dry.

The pre-deployment protector sleeve described above may be used for assemblies in which the soluble polymeric coating covers an expandable member mounted on the catheter.

The pre-deployment protector sleeve may also be used where the soluble polymeric coating further comprises a bioactive substance.

BRIEF DESCRIPTION OF THE DRAWINGS

FIG. 3E shows a cross-sectional view of the sealing member of the protector sleeve of FIG. 2 through line E—E.

FIG. 5 shows a perspective view of a shrink collet which may be used in the fabrication of a protector sleeve.

DETAILED DESCRIPTION OF THE PREFERRED EMBODIMENT

Expandable members, such as inflatable balloons, stents and stents mounted on balloons (e.g., stent deployment assemblies) are generally adapted to function under the substantial expansion pressures during deployment.

However, the surfaces of these structures in their collapsed state are treated as delicate during pre-deployment handling in order to avoid potential damage and/or premature failure. To that end, expandable members, such as balloons are typically protected by a sleeve adapted to slip over and surround the balloon in its collapsed configuration. The sleeve is not removed until the catheter is intended to be used by the physician.

In a preferred mode, the present invention includes a protector sleeve for protecting an expandable member in its collapsed state on a catheter, e.g., a dilatation or stent delivery catheter. The protector sleeve may be used in accordance with preferred embodiments of the present invention to protect expandable members, including balloons, stents, and stent delivery assemblies with a stent(s) mounted over an inflatable balloon, both in their collapsed state, or a self-expanding stent mounted in its collapsed and restrained state, along the distal region of the delivery catheter. Other expandable members within the scope of the present disclosure, include without limitation, wire cages, electrode assemblies and expandable members comprising panels of radioactive or other energy delivery means, and/or sensor arrays. In addition, pharmaceutically active materials, liquid-activated coatings and removable (dissolvable temporary coatings) may be compromised by premature wetting. Indeed, the protector sleeve of the present invention may be suitable for coaxially engaging and protecting any functionality disposed along a catheter in its pre-deployment state.

Figure 1A:
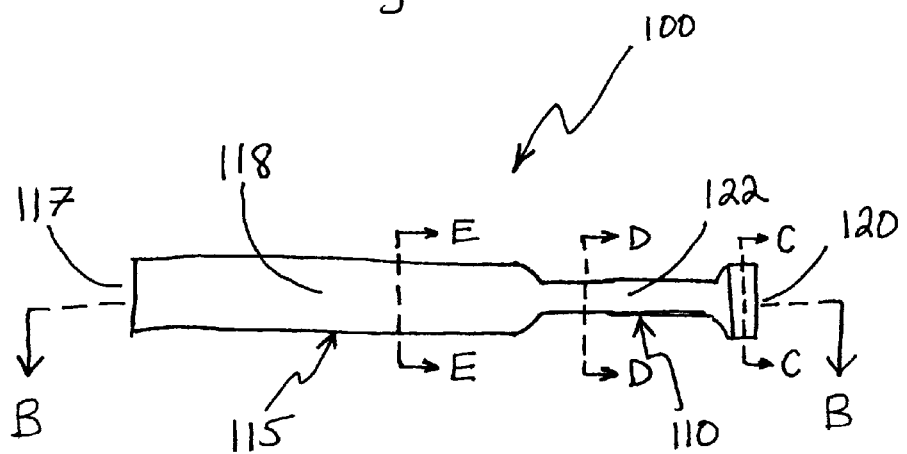
FIG. 1A shows a perspective view of a protector sleeve in accordance with one embodiment of the present invention.
Figure 1B:
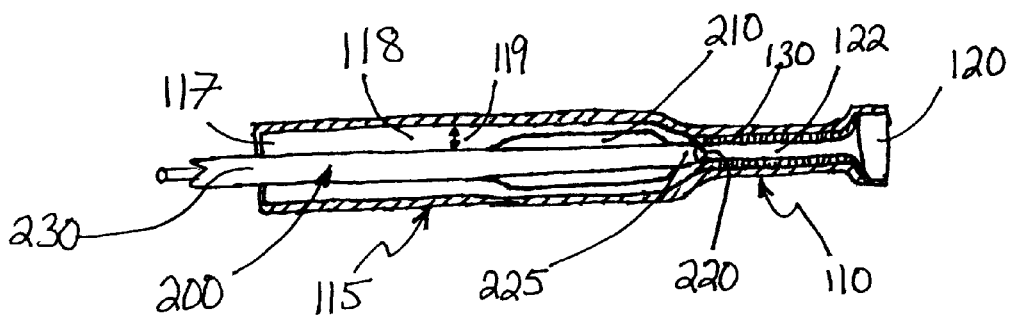
FIG. 1B shows a cross-sectional view of the protector sleeve of FIG. 1A through line B—B.

FIG. 1A shows a protector sleeve in accordance with one embodiment of the present invention. Protector sleeve 100 comprises a proximal portion 115 and a distal portion 110. The proximal portion 115 includes a proximal port 117 and a sleeve lumen 118. The distal portion 110 includes a distal port 120 and a passageway 122. As illustrated in the cross-sectional view (FIG. 1B), the proximal port 117 and sleeve lumen 118 of the proximal portion 115 is sized to slide over the distal portion 200 of a catheter. The illustrated catheter 200 has an expandable member 210 mounted thereon, such that the expandable member 210 is completely covered by the proximal portion 115 of the protector sleeve 100. The catheter 200 also is pictured with an inner lumen 230 (e.g., a guidewire lumen) having a distal port 220. Accordingly, in a preferred mode, the proximal portion has an axial length greater than the length of the expandable member plus any length of the distal tip 225 of the catheter which extends distally beyond the distal margin of the expandable member. Preferably, the sleeve lumen 118 has a diameter just large enough to coaxially engage and accommodate the diameter of the collapsed expandable member 210 on the catheter 200, thereby permitting sliding on and off the distal portion of the catheter. However, the sleeve lumen 118 also has a diameter that is small enough to inhibit and preferably prevent liquids from freely flowing into the coaxial space 119 between the proximal portion 115 of the protector sleeve 100 and the catheter 200 with expandable member 210.

In one preferred aspect of the present embodiment, at least the sleeve lumen of the proximal portion of the protector sleeve is either made from or coated with a hydrophobic material, such that aqueous liquids are inhibited from breaching the coaxial space between the expandable member and the inner wall of the sleeve lumen via capillary action. Such materials are disclosed in greater detail below.

The distal port 120 and passageway 122 are preferably configured to facilitate engagement of a conventional flushing device, e.g. a syringe and needle (not shown). The axial length of the distal portion 110 is preferably longer than a standard irrigation needle, such that the inner lumen 230 of the catheter 200 can be flushed with liquid using a syringe and needle and the distal tip 225 of the catheter and/or the expandable member 210 on the distal end portion of the catheter is not damaged by the needle inserted into the passageway 122. Likewise, the diameter of the passageway 122 is preferably sized to tightly accommodate a typical needle, while facilitating insertion and withdrawal of the needle. The diameter of the passageway 122, however, is preferably sized to provide a fluid tight seal, such that pressurized irrigation fluid from the flushing device only enters the distal port 220 of the inner lumen 230, thereby flushing the inner lumen 230 while not wetting the distal tip 225 of the catheter or the expandable member 210 mounted on the distal portion of the catheter 200. Accordingly, a particularly preferred inner diameter of the passageway is substantially similar to the diameter of the distal port 220 of the catheter's inner lumen 230. The inner lining 130 of the passageway 122 may be coated with an elastomeric material that is hydrophobic in nature, such as silicon, or a natural or synthetic rubber. The elastomeric materials useful in providing a fluid seal are discussed in greater detail below with respect to another embodiment of the present protector sleeve having a separate sealing member.

Figure 1E:
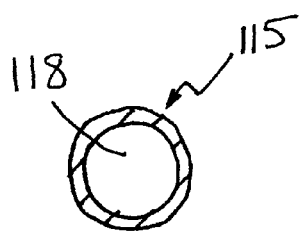
FIG. 1E shows a cross-sectional view of the protector sleeve of FIG. 1A through line E—E.
Figure 1D:
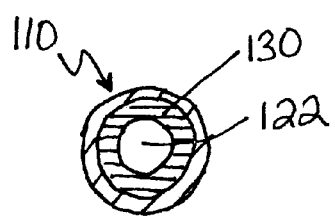
FIG. 1D shows a cross-sectional view of the protector sleeve of FIG. 1A through line D—D.
Figure 1C:
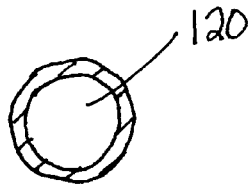
FIG. 1C shows a cross-sectional view of the protector sleeve of FIG. 1A through line C—C.

Cross-sectional views of the protector sleeve 100 are shown in FIGS. 1C, D and E. The cross-sectional view through lines C—C is illustrated in FIG. 1C. The distal port 120 is shown. The diameter is sized to be a convenient target for the operator to find with their flushing device. The cross-sectional view of the passageway 122 of the distal portion 110, through lines D—D, is illustrated in FIG. 1D. The passageway 122 is shown with an inner lining 130, such that the inner diameter of the passageway is smaller than the distal port 120, and as described above, adapted to accommodate and fluidly seal a tubular distal portion (not shown) of a flushing device, e.g., an irrigating needle. The cross-sectional view of the sleeve lumen 118 of the proximal portion 115, through line E—E, is shown in FIG. 1E. Like the cross-section through the distal port region, the diameter of the proximal portion 115 is preferably larger than the diameter of the distal passageway 122. As detailed above, the inner diameter is large enough to coaxially engage and accommodate the diameter of the collapsed expandable member 210 on the catheter 200, thereby permitting sliding on and off the distal portion of the catheter. However, the sleeve lumen 118 preferably has a diameter small enough to inhibit the free flowing of liquids into a coaxial space between the proximal portion 115 of the protector sleeve and the catheter 200 with expandable member 210.

Figure 2:
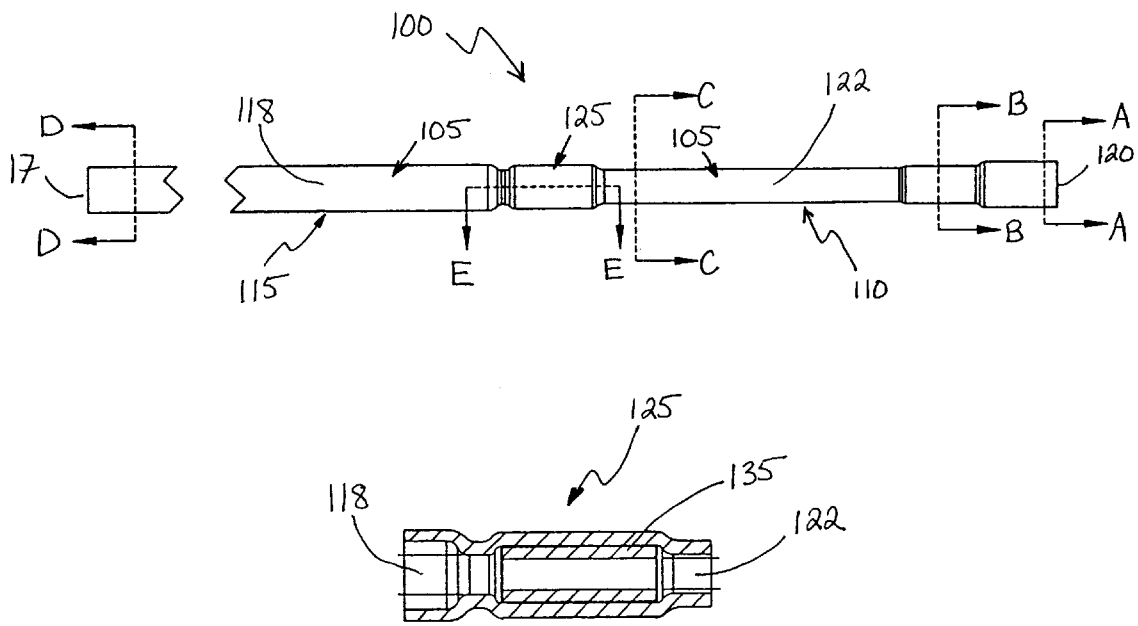
FIG. 2 shows a perspective view of a protector sleeve in accordance with another embodiment of the present invention.

With reference to FIG. 2, another embodiment of the present invention is illustrated. In the illustrated mode, the protector sleeve 100 comprises a sealing member 125 located between the proximal 115 and distal 110 portions of the tubular member 105. Similar to the protector sleeve 100 shown and described with reference to FIGS. 1A–E, the distal portion 110 has a distal port 120 and a passageway 122 and the proximal portion 115 has a proximal port 117 and a sleeve lumen 118.

Figure 3D:
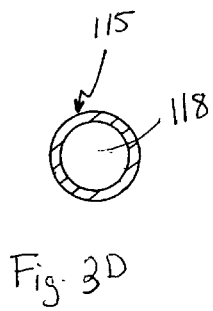
FIG. 3D shows a cross-sectional view of the protector sleeve of FIG. 2 through line D—D.
Figure 3C:
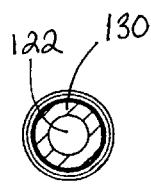
FIG. 3C shows a cross-sectional view of the protector sleeve of FIG. 2 through line C—C.
Figure 3B:
FIG. 3B shows a cross-sectional view of the protector sleeve of FIG. 2 through line B—B.
Figure 3A:
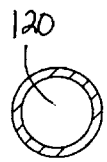
FIG. 3A shows a cross-sectional view of the protector sleeve of FIG. 2 through line A—A.

The distal end of the distal portion 110, however, is further modified in FIG. 2 to include a step-wise decrease in the inner diameter of the passageway 122. Although a tapered decrease may also be employed, the step-wise decrease in inner diameter can be appreciated with reference to FIGS. 3A–C. In FIG. 3A, a cross-sectional view of the distal port region 120 of the distal portion 110, through lines A—A is shown. In FIG. 3B, a cross-section view of the distal portion 110 immediately adjacent to the distal port 120, through lines B—B, is shown, wherein the passageway lumen 122 has an additional lining 127 which causes the inner diameter to decrease. In FIG. 3C, a cross-sectional view of the distal portion 110 and the passageway 122, through lines C—C, is shown, wherein an additional or thicker lining 130 is applied, which in some embodiments may fluidly seal a tubular distal portion (not shown) of a flushing device, e.g., an irrigating needle. In other embodiments, however, a fluid seal between the flushing device and the distal passageway is neither necessary nor preferred. The step-wise decrease in the diameter of the distal portion of the protector sleeve may be varied and/or adapted to accommodate different flushing devices with various fittings. A cross-sectional view of the proximal portion 115, through lines D—D, is shown in FIG. 3D. As discussed above, the sleeve lumen 118 of the proximal portion 115 is sized to slidably receive a catheter having a functionality, e.g., an expandable member, mounted along its distal region.

A cross-sectional view of the sealing member 125, through lines E—E, is illustrated in FIG. 3E. The sealing member 125 includes an elastomeric seal 135 which is adapted to inhibit and preferably prevent liquids introduced through the distal port 120 from passing through the passageway 122 and into the proximal portion 115 of the protector sleeve 100. In the illustrated embodiment, the distal port 120 of the protector sleeve 100 is adapted to fluidly couple via the passageway 122 and through the elastomeric seal 135 of the sealing member 125 to an inner lumen of a catheter (e.g., a guidewire lumen; not shown) to facilitate flushing of the inner lumen with liquids.

Figure 4A:
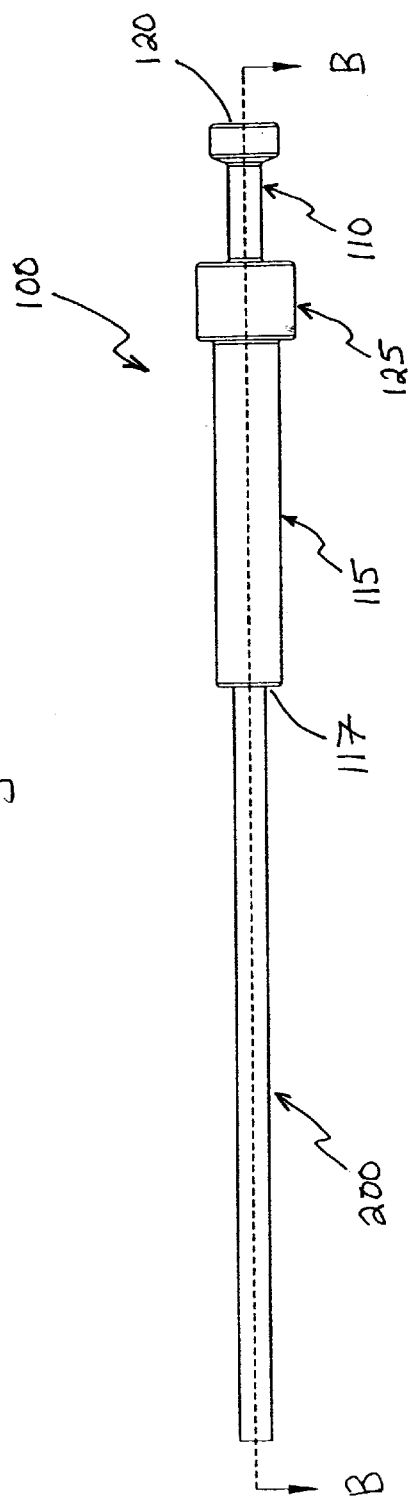
FIG. 4A shows a perspective view of an alternative embodiment of a protector sleeve of the present invention.
Figure 4B:
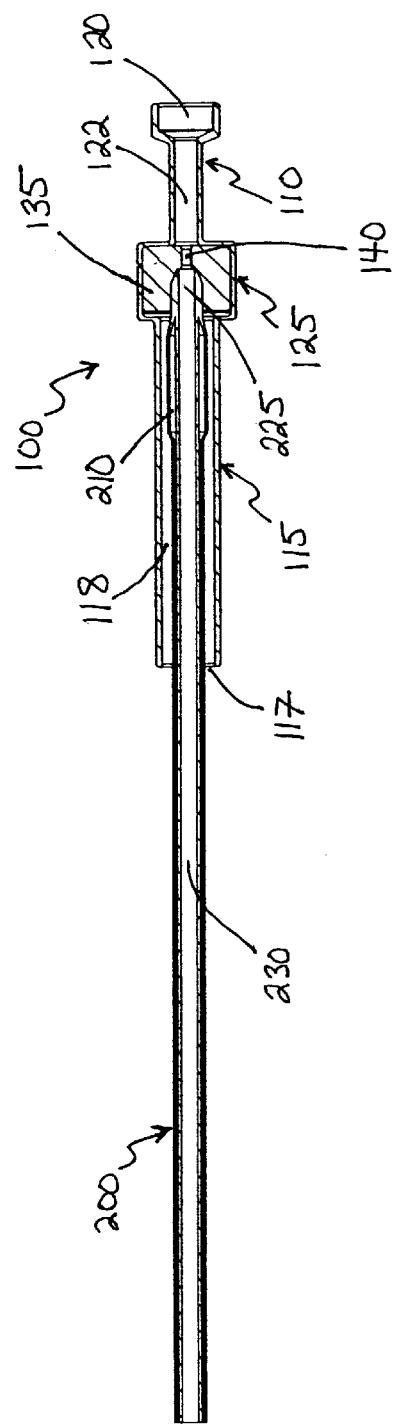
FIG. 4B shows a cross-sectional view of the protector sleeve of FIG. 4A through line B—B.

Another embodiment of the protector sleeve is illustrated in FIGS. 4A–B. A perspective view of a catheter 200 with a protector sleeve 100 on its distal end is shown in FIG. 4A. The protector sleeve in the illustrated embodiment has a distal portion 110 and a proximal portion 115, with a sealing member 125 therebetween. The proximal end of the protector sleeve 100 has a proximal port 117 through which the catheter 200 is slidably engaged.

A cross-sectional view, through line B—B, of the catheter and protector sleeve assembly shown in FIG. 4A is illustrated in FIG. 4B. Like the assembly shown in FIG. 1B, the catheter 200 has an expandable member 210 mounted thereon, such that the expandable member 210 is completely covered by the proximal portion 115 of the protector sleeve 100. The catheter 200 has an inner lumen 230 (e.g., a guidewire lumen). Accordingly, in one mode of the protector sleeve, the proximal portion 115 has an axial length greater than the length of the expandable member 210 plus any length of the distal tip 225 of the catheter which extends distally beyond the distal margin of the expandable member. In the illustrated embodiment, the sleeve lumen 118 has a diameter just large enough to coaxially engage and accommodate the diameter of the collapsed expandable member 210 on the catheter 200, thereby permitting sliding on and off the distal portion of the catheter. However, the sleeve lumen 118 preferably has a diameter small enough to inhibit the uptake of liquids via capillary action into the coaxial space between the proximal portion 115 of the protector sleeve 100 and the catheter 200 with expandable member 210.

The distal port 120 and passageway 122 are preferably configured to facilitate engagement of a conventional flushing device, e.g. a syringe and needle (not shown). The axial length of the distal portion 110 is preferably longer than a standard irrigation needle, such that the inner lumen 230 of the catheter 200 can be flushed with liquid using a syringe and needle and the distal tip 225 of the catheter and/or the expandable member 210 on the distal end portion of the catheter is not damaged by the needle inserted into the passageway 122. In this embodiment, the diameter of the passageway 122 need not sealably accommodate the flushing device, as described in FIG. 1B. Instead, a sealing member 125 with an internal elastomeric seal 135 provides the fluid tight seal that permits irrigation of the inner lumen 230 of the catheter 200 without wetting of the expandable member 210 on the catheter. The proximal portion of the elastomeric seal 135 is adapted to accommodate the distal tip of the catheter 225 in a substantially fluid tight seal, whereas the distal portion of the elastomeric seal 135 has an access lumen 140 that fluidly couples the inner lumen 230 of the catheter with the passageway 122 of the distal portion 110 of the protector sleeve, such that irrigation fluid from the flushing device in the passageway 122 only has access via the access lumen 140 to the inner lumen 230 of the catheter.

The dimensions and configuration of the protector sleeve in accordance with a preferred embodiment of the present invention are such that removal by the physician prior to deployment is via the simple standard method of pulling the protector sleeve off over the distal end of the catheter. In addition, the coaxial space between the catheter and protector sleeve is preferably small enough to prevent liquids from freely flowing into the gap, yet large enough to permit removal from the catheter without damage to the expandable member. The use of hydrophobic tubing materials or coatings may further prevent infiltration of aqueous liquids into the coaxial space via capillary action. The length of the proximal portion of the sleeve should be greater than the length of the expandable member and the length of the distal portion should be greater than the length of the intended flushing device. Generally, the proximal portion is preferably at least 5 mm longer than the total length of catheter/expandable member to be kept dry and the distal portion is preferably about 0.25 inches longer than the inserting tubular section of the flushing device. In embodiments that incorporate a separate sealing member, the length of the sealing member is preferably about 0.125 inches.

The inner diameter of the protector sleeve is preferably in the range of about 0.100 to about 0.008 inches, and more preferably in the range of about 0.050 to about 0.010 inches, and most preferably about 0.032 inches. The outer diameter is preferably in the range of about 0.200 about 0.010 inches, and more preferably in the range of about 0.080 to about 0.030 inches, and most preferably about 0.055 inches. The inner diameter of elastomeric seal is preferably slightly smaller than the outer diameter of the device just distal to the area to be kept dry. In one preferred embodiment, the ID of the elastomeric seal is about 0.025 inches.

The tubular member and elastomeric seal of the protector sleeve are preferably made of a hydrophobic material to resist capillary action of liquids between the catheter and protector sleeve. Alternatively, the components may have a coating made from a hydrophobic material or the protector sleeve may be treated, so as to behave as a hydrophobic material.

Any suitable material that is compatible for use in medical or therapeutic applications may be used to make the tubular member of the protector sleeve. Such materials include, without limitation, TEFLON, silicones, parylene, and other hydrophobic materials. In a preferred embodiment, components of the tubular member are made from FEP shrink tubing.

The components of the protector sleeve may be made from a single continuous material, such as by extrusion or molding methods known to those of skill in the art. Alternatively, the proximal and distal portions and the sealing member may be joined after fabrication by adhesive bonding, welding, or simply pressing together in a manner that insures a secure junction.

In some preferred embodiments, the proximal portion of the protector sleeve may be tapered, the degree of taper being selected to closely surround the expandable member while permitting the protector sleeve to be slipped on to and off of the expandable member with relative ease. In catheters where there is little or no difference in the profile of the proximal and distal regions, the protector sleeve may have very little if any taper.

Elastomers appropriate for use in fabricating the elastomeric seal include, without limitation, natural and synthetic rubbers, polyurethanes, polyolefins, such as grafted EPDM polymers, thermoplastic elastomers such as styrene block copolymers, silicones, and fluorocarbon elastomers. In general, any elastomer that is compatible for use in medical or therapeutic applications can be employed. Preferably, the elastomer is capable of withstanding multiple sterilization cycles. Further, preferred elastomeric materials are capable of forming an oxygen- and water-excluding barrier between an internal fluid environment and the external environment. The elastomers are preferably also be able to withstand potential damage caused by deployment and irrigation devices (e.g., needles used to flush the guidewire lumens). Elastomers can be thermoplastic or thermoset elastomers which can be cured or cross-linked by any method known in the art. Lubricating materials may also be added to the elastomer. In one preferred embodiment, the elastomeric seal is made of silicone.

The seal can be formed by plastic injection molding or extrusion. The seal may be slightly tapered toward its proximal end, and preferably has a opening which is substantially the same as the size of the outer diameter of the catheter, so that it forms a fluid-tight seal with the cylindrical wall of distal tip of the catheter.

In an alternative embodiment, the protector sleeve may be made of a plurality of longitudinal sleeves, enhancing compression of the balloon and providing a better profile.

The protector sleeve is suitable for covering and protecting the distal portion of any catheter. It may be of any length consistent with its purpose in protecting a functional member mounted on a catheter. Expandable members of any length may be accommodated by the protector sleeve. In its pre-deployed collapsed state, the expandable member (e.g., balloon) may be folded or otherwise collapsed. For inflatable balloons, the catheters typically include an inflation port and an inflation lumen contained in the catheter shaft and opening into the balloon or a passageway or passageways formed between the outside of the catheter shaft and the membrane forming the balloon. The catheter may also be associated with a source of pressurized fluid (gas or liquid) for inflating the balloon.

The details and mechanics of balloon inflation and specific overall catheter construction will vary according to the design of the catheter, and are known in the art. All of these variations are acceptable for use with the various embodiments of the protector sleeves disclosed herein.

In one embodiment of the current invention, a stent is covered with a polymeric coating. The material used to form the polymeric coating can include, but is not limited to, polyvinyl pyrrolidone, polyethylene glycol, polyethylene oxide, polyethylene acetate, polyvinyl alcohol, polyacrylic acid, polymethacrylic acid, polyacrylamide, hydrophilic soft segment urethane, gum Arabic, gum tragacanth, or any combination thereof. The polymeric coating is preferably dissolvable or degradable within the body. As a result, it serves to protect the stent during handling and insertion in the body, but it dissolves or degrades to allow the stent to be deployed at the implantation site. The polymeric coating may also contain a bioactive substance for controlled release at the site of stenosis as the polymer dissolves.

In one method of preparing the coating, the material used for the coating is first dissolved in a solvent, such as 100% ethanol, to obtain a solution which is 20% concentration by weight. The solution is then applied to the stent by using techniques known to those skilled in the art, such as the process disclosed in U.S. Pat. No. 5,234,457, which is hereby incorporated by reference, in which the stent is rotated on a mandrel as the solution is poured over the stent. The stent is then air cured to form the protective polymeric coating.

Such a protective polymeric coating would deteriorate and/or dissolve prematurely if exposed to a liquid environment during pre-deployment handling and flushing of the catheter. Thus, the protective sleeve in accordance with another preferred embodiment of the present invention it adapted to protect a liquid-soluble polymeric coating from premature wetting.

A protector sleeve in accordance with one preferred embodiment of the present invention may be fabricated by any methods known in the art. In one preferred method, fabrication involved the following steps. First, cutting guides were obtained or prepared having the desired dimensions. For example, the inventors prepared two cutting guides, one for cutting the protector sleeve tubing and one for cutting an elastomic seal. The first comprises a length (3.985 inches) of 17 gauge 316 stainless steel (SS) tubing (0.042 ID×0.058 OD), fixed by spot welding within a length (0.985 inches) of a 15 gauge 316 SS tubing (0.060 ID×0.072 OD) is made. Thus, a 3.000 inch length of the inner 316 SS tubing extends beyond one end of the shorter 15 gauge tubing. The second cutting guide for cutting a sealing member (e.g., a length of silicon tubing) comprises a length (1.500 inches) of 0.026 inch 316 stainless steel wire, fixed by spot welding within a length (1.375 inches) of a 19 gauge 316 stainless steel tubing (0.027 ID×0.042 OD). Thus, a 0.125 inch length of the inner 316 SS wire extends beyond one end of the cylindrical tubing.

An FEP tubing was slid over the inner 17 gauge tubing of the first cutting guide until the FEP tubing reached the stop (the outer 15 gauge tubing). The FEP tubing slid over the inner member of the cutting guide with no obstructions. The FEP tubing (a 3 inch length) was cut using a straight razor at the end of the cutting guide by slowing rotating the tubing while applying pressure on the razor. Subsequently, the FEP tubing of predetermined length (3 inches in the example) was removed from the cutting guide.

Similarly, silicone tubing was slid over the silicon cutting guide until the tubing reached the stop (i.e., 0.125 inches). The tubing slid over the cutting guide with no obstruction. The silicon tubing was cut at the end of the cutting guide by slowly revolving the assembly as pressure was applied to the cutting edge. The silicon sealing member was removed from the cutting guide.

Additional tooling was also prepared by the inventor for assembling a protector sleeve in accordance with one preferred embodiment of the present invention. A shrink mandrel (a 10 inch long, 0.026 inch thick 316 SS wire) was prepared and polished. A positioning collet was made comprising a 2.250 inch length of 19 gauge 316 SS tubing (0.027 ID×0.042 OD) and a 0.500 inch length of 0.026 inch thick 316 SS wire. A length (0.250 inches) of the wire was slid into the tubing and spot welded in place, leaving 0.250 inches of the wire extending from the tubing. A shrink collet was also prepared. The shrink collet 300 is illustrated in FIG. 5. It comprises a length (0.985 inches) of outer tubing 310 (0.060 ID×0.072 ID), a length (1.490 inches) of intermediate tubing 320 (0.042 ID×0.058 OD), a length (1.740 inches) of inner tubing 330 (0.027 ID×0.042 OD), and a length (0.5 inches) of 316 SS wire 340 (0.026 inches). Heat-shrinking the FEP tubing over the shrink collet yielded a protector sleeve with a step-wise change in diameter, as illustrated with reference to FIG. 2.

The silicon tubing was slid onto the shrink mandrel. Then the positioning collet was used to push the tubing into location. The FEP tubing was slid onto the shrink collet and the tubing and collet assembly are placed onto the shrink mandrel. The assembly was heated using a heat gun with a heated airflow while slowly rotating the assembly. After the assembly was cooled, the shrink mandrel and shrink collet were removed from protector sleeve.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A protector sleeve for protecting an expandable member on a catheter having an inner lumen and a distal tip, wherein the expandable member is in a collapsed state prior to deployment, said protector sleeve comprising:
   a tubular member having proximal and distal portions and a sealing member therebetween, wherein said proximal and distal portions and said sealing member are formed from a single continuous material, said proximal portion being adapted to slidably engage the catheter and cover the collapsed expandable member, wherein a coaxial separation between the proximal portion of the tubular member and the collapsed expandable member is sized to substantially prevent liquids from entering the coaxial separation;
   wherein said sealing member is adapted to engage the distal tip of the catheter, such that a substantially fluid-tight seal is created between the sealing member and the distal tip; and
   said distal portion of the tubular member defining a passageway adapted to fluidly couple with the inner lumen of the catheter, such that the inner lumen may be flushed with a liquid while the collapsed expandable member proximal to the sealing member remains substantially dry.

2. The protector sleeve of claim 1, wherein said distal portion of the tubular member is sufficiently long to prevent a flushing device from contacting the distal tip of the catheter.

3. The protector sleeve of claim 1, wherein the collapsed expandable member comprises an inflatable balloon in a radially collapsed state.

4. The protector sleeve of claim 1, wherein the collapsed expandable member comprises a expandable stent in a radially collapsed state.

5. A pre-deployment protector sleeve for protecting a soluble polymeric coating applied to a portion of a catheter having an inner lumen and a distal tip, comprising:
   a tubular member having proximal and distal portions and a sealing member therebetween, said proximal portion being adapted to slidably engage the catheter and cover the polymeric coating, wherein a coaxial separation between the proximal portion of the tubular member and the polymeric coating is sized to substantially prevent liquids from entering the coaxial separation;
   wherein said sealing member is adapted to engage the distal tip of the catheter, such that a substantially fluid-tight seal is created between the sealing member and the distal tip; and
   said distal portion of the tubular member defining a passageway adapted to fluidly couple with the inner lumen of the catheter, such that the inner lumen may be flushed with a liquid while the polymeric coating proximal to the sealing member remains substantially dry;
   wherein said soluble polymeric coating covers an expandable member mounted on the catheter.

6. A pre-deployment protector sleeve for protecting a soluble polymeric coating applied to a portion of a catheter having an inner lumen and a distal tip, comprising:
   a tubular member having proximal and distal portions and a sealing member therebetween, said proximal portion being adapted to slidably engage the catheter and cover the polymeric coating, wherein a coaxial separation between the proximal portion of the tubular member and the polymeric coating is sized to substantially prevent liquids from entering the coaxial separation;
   wherein said sealing member is adapted to engage the distal tip of the catheter, such that a substantially fluid-tight seal is created between the sealing member and the distal tip; and
   said distal portion of the tubular member defining a passageway adapted to fluidly couple with the inner lumen of the catheter, such that the inner lumen may be flushed with a liquid while the polymeric coating proximal to the sealing member remains substantially dry;
   wherein said soluble polymeric coating further comprises a bioactive substance.

7. A method for protecting an expandable member mounted on a catheter having an inner lumen and a distal tip, wherein the expandable member is in a collapsed state prior to deployment, the method comprising:
   providing a protector sleeve comprising a tubular member having proximal and distal portions and a sealing member therebetween, wherein said sealing member is adapted to engage the distal tip of the catheter, such that a substantially fluid-tight seal is created between the sealing member and the distal tip, and wherein said distal portion of the tubular member defines a passageway adapted to fluidly couple with the inner lumen of the catheter, such that the inner lumen may be flushed with a liquid while the collapsed expandable member proximal to the sealing member remains substantially dry; and
   sliding the protector sleeve over the collapsed expandable member, such that the distal tip of the catheter engages the sealing member.

8. The method of claim 7, further comprising inserting a portion of a flushing device into the passageway of said distal portion, and flushing the inner lumen of the catheter.

* * * * *

UNITED STATES PATENT AND TRADEMARK OFFICE
CERTIFICATE OF CORRECTION

PATENT NO. : 6,749,584 B2  Page 1 of 1
APPLICATION NO. : 10/010787
DATED : June 15, 2004
INVENTOR(S) : Leonard F. Briggs and Tom Steinke It is certified that error appears in the above-identified patent and that said Letters Patent is hereby corrected as shown below:

Delete Figure 2, and insert FIG. 2 as shown.

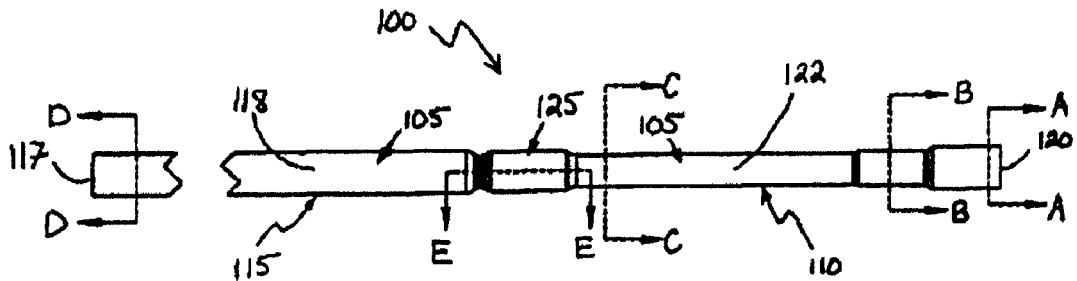

In Column 2, line 42, please delete "portions The" and insert -- portions. The -- therefore.

In Column 11, line 66, Claim 4, after "comprises' delete "a" and insert -- an --, therefore.

Signed and Sealed this

Fifteenth Day of January, 2008

JON W. DUDAS
*Director of the United States Patent and Trademark Office*